(12) United States Patent
Kshirsagar et al.

(10) Patent No.: US 9,719,812 B2
(45) Date of Patent: Aug. 1, 2017

(54) GAS SENSOR HOUSING

(71) Applicants: Abhijeet Vikram Kshirsagar, Pune (IN); Chinmaya Rajiv Dandekar, Pune (IN); Amit Barjatya, Barnagar (IN)

(72) Inventors: Abhijeet Vikram Kshirsagar, Pune (IN); Chinmaya Rajiv Dandekar, Pune (IN); Amit Barjatya, Barnagar (IN)

(73) Assignee: Cooper Technologies Company, Houston, TX (US)

( * ) Notice: Subject to any disclaimer, the term of this patent is extended or adjusted under 35 U.S.C. 154(b) by 175 days.

(21) Appl. No.: 14/821,546

(22) Filed: Aug. 7, 2015

(65) Prior Publication Data

US 2017/0038229 A1 Feb. 9, 2017

(51) Int. Cl.
*G01N 21/00* (2006.01)
*G01D 11/24* (2006.01)

(52) U.S. Cl.
CPC .................................. *G01D 11/245* (2013.01)

(58) Field of Classification Search
CPC . G01N 21/1702; G01N 21/1704; G01N 21/00
USPC .............................................. 73/24.01, 24.02
See application file for complete search history.

(56) References Cited

U.S. PATENT DOCUMENTS

| 5,817,922 A | 10/1998 | Rapp et al. |
| 5,880,353 A | 3/1999 | Graser et al. |
| 8,117,897 B2 | 2/2012 | Schropp, Jr. et al. |

FOREIGN PATENT DOCUMENTS

WO 2006071171 7/2006

OTHER PUBLICATIONS

N. Listvina, International Search Report and Written Opinion issued in PCT/US2016/045187, completion date Oct. 26, 2016, mailing date Nov. 10, 2016, 6 pages, Federal Institute of Industrial Property, Moscow, Russia.

*Primary Examiner* — Lisa Caputo
*Assistant Examiner* — Jamel Williams
(74) *Attorney, Agent, or Firm* — King & Spalding LLP

(57) ABSTRACT

A housing for a gas sensor module is described herein. The housing can include a first portion and a second portion. The first portion can include at least one wall forming a cavity having a first cavity portion and a second cavity portion. The first portion can also include an inlet tube coupling feature and a distribution channel disposed adjacent to the first cavity portion. The first portion can further include an outlet tube coupling feature and a receiving channel disposed adjacent to the second cavity portion. The second portion can include a tuning fork coupling feature disposed adjacent to the second cavity.

20 Claims, 4 Drawing Sheets

GAS SENSOR HOUSING

TECHNICAL FIELD

Embodiments described herein relate generally to gas sensors, and more particularly to systems, methods, and devices for housings for optical gas sensors.

BACKGROUND

The detection and measurement of trace gas concentrations is important for both the understanding and monitoring of a wide variety of applications, such as environmental monitoring, industrial process control analysis, combustion processes, detection of toxic and flammable gases, as well as explosives. For example, trace gas sensors capable of high sensitivity and selectivity can be used in atmospheric science for the detecting and monitoring of different trace gas species including greenhouse gases and ozone, and in breath diagnostics, for detection and monitoring of nitric oxide, ethane, ammonia and numerous other biomarkers. As another example, in gas-to-grid applications, methane generated from a biogas process is tested for impurities (e.g., hydrogen sulfide or $H_2S$) to determine whether the methane is pure enough to be mixed directly with natural gas.

SUMMARY

In general, in one aspect, the disclosure relates to a housing for a gas sensor module. The housing can include a first portion and a second portion coupled to the first portion. The first portion of the housing can include at least one first wall forming a first cavity, where the first cavity has a first cavity portion and a second cavity portion. The first portion of the housing can also include an inlet tube coupling feature disposed at a first location in the at least one first wall, where the first location is adjacent to the first cavity portion of the first cavity. The first portion of the housing can further include an outlet tube coupling feature disposed in a second location in the at least one first wall, where the second location is adjacent to the second cavity portion of the first cavity. The first portion of the housing can also include a distribution channel disposed at a third location in the at least one first wall, where the third location is adjacent to the first cavity portion of the first cavity. The first portion of the housing can further include a receiving channel disposed in a fourth location in the at least one first wall, where the fourth location is adjacent to the second cavity portion of the first cavity. The second portion of the housing can include at least one second wall forming a second cavity. The second portion of the housing can also include a tuning fork coupling feature disposed at a fifth location in the at least one second wall, where the fifth location is adjacent to the second cavity.

In another aspect, the disclosure can generally relate to a gas sensor. The gas sensor can include a housing. The housing of the gas sensor can include at least one wall forming a first cavity and a second cavity, where the first cavity has a first cavity portion and a second cavity portion. The housing of the gas sensor can also include an inlet tube coupling feature disposed at a first location in the at least one wall, where the first location is adjacent to the first cavity portion of the first cavity. The housing of the gas sensor can further include an outlet tube coupling feature disposed in a second location in the at least one wall, where the second location is adjacent to the second cavity portion of the first cavity. The housing of the gas sensor can also include a tuning fork coupling feature disposed at a third location in the at least one wall, where the third location is adjacent to the second cavity. The housing of the gas sensor can further include a distribution channel disposed between the first cavity portion of the first cavity and the second cavity. The housing of the gas sensor can also include a receiving channel disposed between the second cavity portion of the first cavity and the second cavity. The gas sensor can also include an inlet tube coupled to the inlet tube coupling feature, and an outlet tube coupled to the outlet tube coupling feature. The gas sensor can further include a tuning fork coupled to the tuning fork coupling feature.

These and other aspects, objects, features, and embodiments will be apparent from the following description and the appended claims.

BRIEF DESCRIPTION OF THE DRAWINGS

The drawings illustrate only example embodiments of housings for optical gas sensors and are therefore not to be considered limiting of its scope, as housings for optical gas sensors may admit to other equally effective embodiments. The elements and features shown in the drawings are not necessarily to scale, emphasis instead being placed upon clearly illustrating the principles of the example embodiments. Additionally, certain dimensions or positionings may be exaggerated to help visually convey such principles. In the drawings, reference numerals designate like or corresponding, but not necessarily identical, elements.

DETAILED DESCRIPTION OF EXAMPLE EMBODIMENTS

Figure 1:
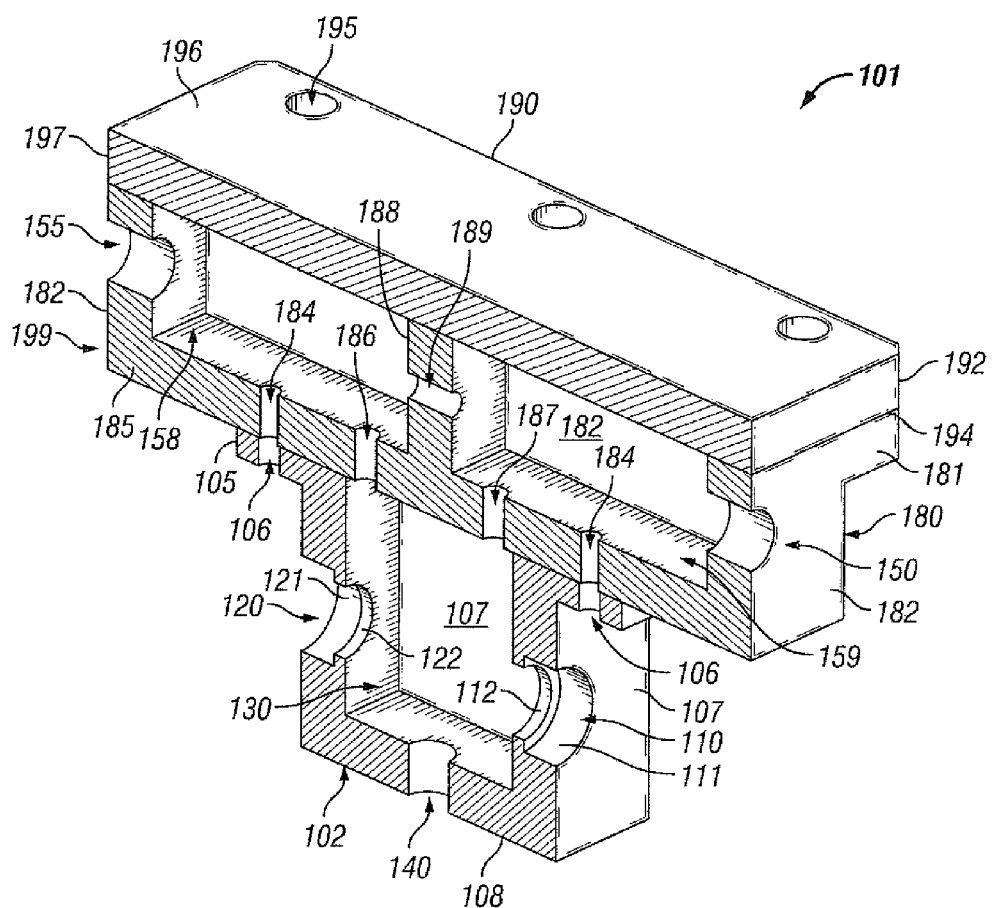
FIG. 1 shows a cross-sectional top-side perspective view of a gas sensor housing in accordance with certain example embodiments.

The example embodiments discussed herein are directed to systems, apparatuses, and methods related to housings for optical gas sensors. Optical gas sensors can have a number of configurations and use a number of technologies. For example, a quartz-enhanced photo-acoustic spectroscopic (QEPAS) sensor can have an optical irradiation at a gas-specific wavelength directed through a gap between the prongs of a quartz tuning fork (QTF) vibrating at its resonating frequency. The optical energy is absorbed and released by the gas, causing a change in the resonant frequency of the QTF. The amount of change in the resonant frequency of the QTF is proportional to the concentration of the gas molecules.

While example embodiments are described herein as being directed to optical gas sensors, example embodiments can also be used with other types of sensors. Further, optical gas sensors that can be used with example embodiments can have any of a number of configurations not shown or described herein. As described herein, a user can be any person that interacts with example optical gas sensors.

Examples of a user may include, but are not limited to, a consumer, an operations specialist, a gas engineer, a supervisor, a consultant, a contractor, an operator, and a manufacturer's representative.

In one or more example embodiments, example housings for optical gas sensors are subject to meeting certain standards and/or requirements. For example, the International Electrotechnical Commission (IEC) sets standards, such as IEC 60079-28 that applies to optical gas sensors, with which example housings must comply to be used in field applications. Examples of other entities that set applicable standards and regulations include, but are not limited to, the National Electrical Manufacturers Association (NEMA), the National Electric Code (NEC), the Institute of Electrical and Electronics Engineers (IEEE), and Underwriters Laboratories (UL).

In some cases, the example embodiments discussed herein can be used in any type of hazardous environment, including but not limited to an airplane hangar, a drilling rig (as for oil, gas, or water), a production rig (as for oil or gas), a refinery, a chemical plant, a power plant, a mining operation, a wastewater treatment facility, and a steel mill. The housings for optical gas sensors (or components thereof) described herein can be physically placed in and/or used with corrosive components (e.g., gases). In addition, or in the alternative, example housings for optical gas sensors (or components thereof) can be subject to extreme heat, extreme cold, moisture, humidity, dust, and other conditions that can cause wear on the housings for optical gas sensors or portions thereof.

In certain example embodiments, the housings for optical gas sensors, including any components and/or portions thereof, are made of one or more materials that are designed to maintain a long-term useful life and to perform when required without mechanical and/or other types of failure. Examples of such materials can include, but are not limited to, aluminum, stainless steel, fiberglass, glass, plastic, ceramic, nickel-based alloys, and rubber. Such materials can be resistant to corrosion, corrosive materials (e.g., $H_2S$ gas) and other harmful effects that can be caused by the test gas, the tested gas, and/or the environment in which the gas sensor housing is exposed.

Any components (e.g., inlet tube coupling feature, receiving channel) of example housings for optical gas sensors, or portions thereof, described herein can be made from a single piece (as from a mold, injection mold, die cast, or extrusion process). In addition, or in the alternative, a component (or portions thereof) can be made from multiple pieces that are mechanically coupled to each other. In such a case, the multiple pieces can be mechanically coupled to each other using one or more of a number of coupling methods, including but not limited to epoxy, welding, fastening devices, compression fittings, mating threads, and slotted fittings. One or more pieces that are mechanically coupled to each other can be coupled to each other in one or more of a number of ways, including but not limited to fixedly, hingedly, removeably, slidably, and threadably.

Components and/or features described herein can include elements that are described as coupling, fastening, securing, abutting, or other similar terms. Such terms are merely meant to distinguish various elements and/or features within a component or device and are not meant to limit the capability or function of that particular element and/or feature. For example, a feature described as a "coupling feature" can couple, secure, fasten, abut, and/or perform other functions aside from, or in addition to, merely coupling.

A coupling feature (including a complementary coupling feature) as described herein can allow one or more components (e.g., a housings) and/or portions of optical gas sensors to become mechanically and/or electrically coupled, directly or indirectly, to another portion of the optical gas sensor. A coupling feature can include, but is not limited to, a clamp, a portion of a hinge, an aperture, a recessed area, a protrusion, a slot, a spring clip, a tab, a detent, a threaded coupling, and mating threads. One portion of an example optical gas sensor can be coupled to another portion of the optical gas sensor by the direct use of one or more coupling features. In addition, or in the alternative, a portion of an example optical gas sensor can be coupled to another portion of the optical gas sensor using one or more independent devices that interact with one or more coupling features disposed on a component of the optical gas sensor. Examples of such devices can include, but are not limited to, a pin, a hinge, a fastening device (e.g., a bolt, a screw, a rivet), and a spring.

One coupling feature described herein can be the same as, or different than, one or more other coupling features described herein. A complementary coupling feature as described herein can be a coupling feature that mechanically couples, directly or indirectly, with another coupling feature. For any figure shown and described herein, one or more of the components may be omitted, added, repeated, and/or substituted. Accordingly, embodiments shown in a particular figure should not be considered limited to the specific arrangements of components shown in such figure.

Example embodiments of housings for optical gas sensors will be described more fully hereinafter with reference to the accompanying drawings, in which example housings for optical gas sensors are shown. Housings for optical gas sensors may, however, be embodied in many different forms and should not be construed as limited to the example embodiments set forth herein. Rather, these example embodiments are provided so that this disclosure will be thorough and complete, and will fully convey the scope of housings for optical gas sensors to those of ordinary skill in the art. Like, but not necessarily the same, elements (also sometimes called components) in the various figures are denoted by like reference numerals for consistency.

Terms such as "top", "bottom", "left", "right", "inner," "outer," "end," "distal", "proximal", "first", and "second" are used merely to distinguish one component (or part of a component or state of a component) from another. Such terms are not meant to denote a preference or a particular orientation, and are not meant to limit embodiments of housings for optical gas sensors. In the following detailed description of the example embodiments, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Also, the names given to various components described herein are descriptive of example embodiments and are not meant to be limiting in any way. Those skilled in the art will appreciate that a feature and/or component shown and/or described in one embodiment (e.g., in a figure) herein can be used in another embodiment (e.g., in any other figure) herein, even if not expressly shown and/or described in such other embodiment.

Figure 2A:
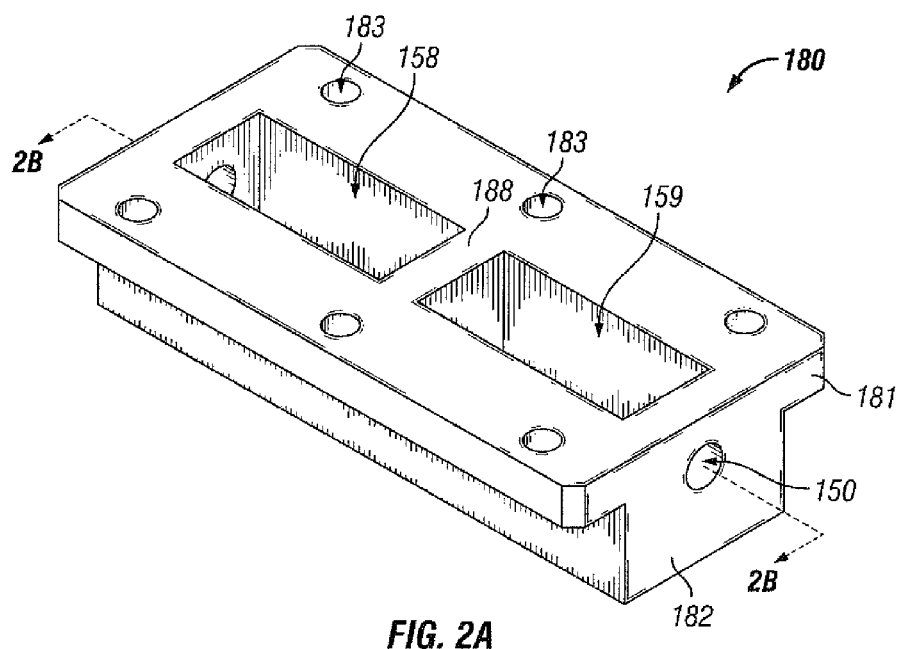
FIGS. 2A and 2B show a portion of a gas sensor housing of FIG. 1 in accordance with certain example embodiments.
Figure 2B:
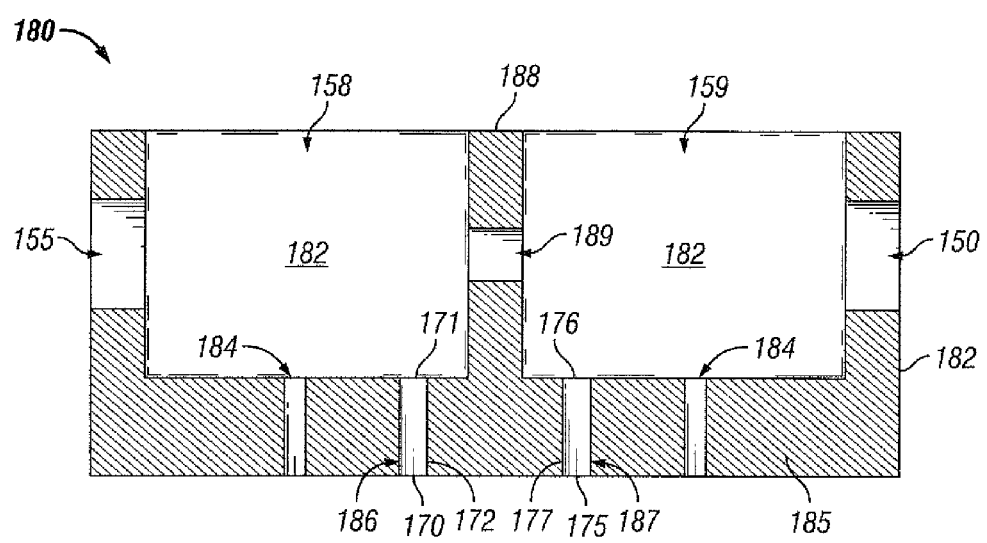

FIG. 1 shows a cross-sectional top-side perspective view of a gas sensor housing 101 in accordance with certain example embodiments. FIGS. 2A and 2B show the main body 180 of the top portion 199 of the gas sensor housing

Figure 3:
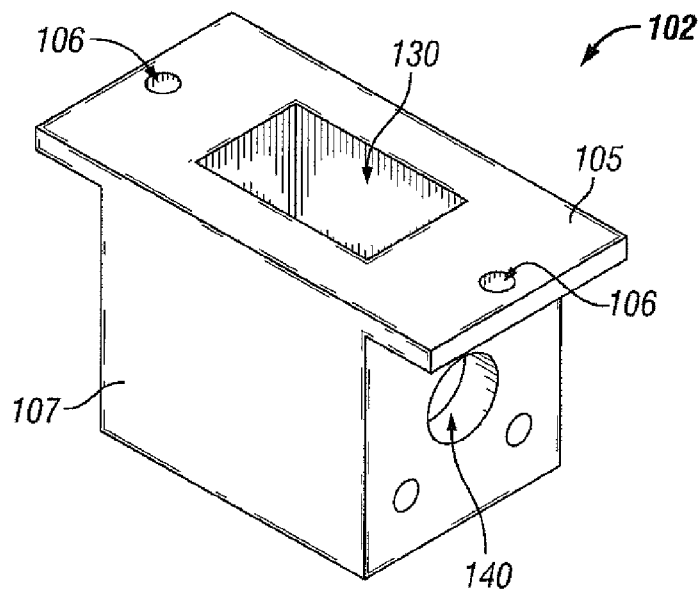
FIG. 3 shows a top-side perspective view of another portion of the gas sensor housing of FIG. 1 in accordance with certain example embodiments.

101 of FIG. 1 in accordance with certain example embodiments. FIG. 3 shows a top-side perspective view of the bottom portion 102 of the gas sensor housing 101 of FIG. 1 in accordance with certain example embodiments.

Referring to FIGS. 1-3, the gas sensor housing 101 can have multiple (e.g., two, three, four) portions. For example, as shown in FIG. 1, the gas sensor housing 101 can include a top portion 199 and a bottom portion 102. In such a case, each portion of the gas sensor housing 101 can have at least one cavity. In this example, the top portion 199 has a cavity (defined by cavity portion 158 and cavity portion 159), and the bottom portion 102 has a cavity 130. The top portion 199 and the bottom portion 102 of the housing 101 can have any of a number of shapes and sizes that are the same or different than each other. For example, the top portion 199 and the bottom portion 102 of the housing 101 shown in FIGS. 1-3 are rectangular parallelepiped in shape, with the top portion 199 being wider than the bottom portion 102.

The gas sensor housing 101 can be configured to perform any measurements of the gas being tested (also called the test gas herein). For this to occur, the various portions (e.g., top portion 199, bottom portion 102) of the example housing 101 can be coupled to each other in such a way that one portion (e.g., top portion 199) delivers the test gas to another portion (e.g., bottom portion 102), and also receives the tested gas (the test gas that has been tested) from the other portion of the housing 101. The example housing 101 (or portion thereof) can include at least one wall that forms a cavity. For example, the top portion 199 of the housing 101 in this case has a top wall 190 (also sometimes called a top plate 190), a side wall 182, and a bottom wall 185 that forms the cavity of the top portion 199. As another example, the bottom portion 102 of the housing 101 in this case has a side wall 107 and a bottom wall 108 that forms the cavity 130.

The cavity of the top portion 199 and the cavity 130 of the bottom portion 102 can be completely enclosed, substantially enclosed, or partially enclosed. For example, if the top plate 190 is removed, the cavity of the top portion 199 would be partially enclosed. As another example, if the bottom portion 102 and the top portion 199 of the housing 101 are detachable, the bottom portion 102 shown in FIGS. 1 and 3 would be partially enclosed because the top wall 105 of the bottom portion 102 cover the cavity 130, and so the cavity 130 is instead enclosed by the bottom wall 185 of the top portion 199 when the top portion 199 and the bottom portion 102 are coupled to each other.

In certain example embodiments, the cavity of the top portion 199 has multiple (e.g., two, three, four) portions. For example, in this case the cavity of the top portion 199 is divided into a first cavity portion 158 and a second cavity portion 159. When the cavity of the top portion 199 (or any other portion of the housing 101) has multiple cavity portions, each cavity portion can be virtually or physically separated from other cavity portions of the cavity of the top portion 199. For example, in this case, the first cavity portion 158 and the second cavity portion 159 are physically separated from each other by a partition 188. In such a case, the partition 188 can have or include one or more of a number of characteristics. Examples of such characteristics can include, but are not limited to, a solid configuration, a porous material, a non-porous material, a mesh, and an orifice (such as orifice 189).

When the cavity portions of the top portion 199 of the housing 101 of FIGS. 1-2B are physically separated from each other by the partition 188, the partition 188 can substantially isolate one cavity portion (e.g., cavity portion 158) from the other cavity portions (e.g., cavity portion 159) of the top portion 199 of the housing 101. A partition 188 can be temporary or permanent with respect to its position in the cavity of the top portion 199. There can be multiple partitions 188. In addition, or in the alternative, a partition 188 can have no orifice or multiple orifices 189. An orifice 189 can traverse some or all of the thickness of a partition 188.

The partition 188 can also help reduce and/or control the flow rate and/or turbulent flow of the test gas, which in turn can control the flow of the test gas sent to another portion (e.g., bottom portion 102) of the housing 101. The partition 188 can also help regulate one or more of a number of parameters (e.g., pressure) within the cavity of the top portion 199. If the cavity of the top portion 199 has multiple cavity portions, the shape and size of one portion of the cavity can be the same as, or different than, the shape and size of the other portions of the cavity. For example, in this case, cavity portion 158 can have substantially the same shape and size as the cavity portion 159.

In certain example embodiments, the top portion 199 is coupled to one or more other portions of the housing 101. For example, in this case, top portion 199 is coupled to the bottom portion 102 of the housing 101. The top portion 199 can be coupled to the bottom portion 102 using one or more of a number of coupling features 184 (sometimes called a bottom portion coupling feature 184). For example, in FIGS. 1-2B, the coupling features 184 are two apertures that traverse the thickness of the bottom wall 185 of the top portion 199 and that are disposed substantially equidistantly from the partition 189 that divides the cavity portion 158 from the cavity portion 159.

Figure 4:
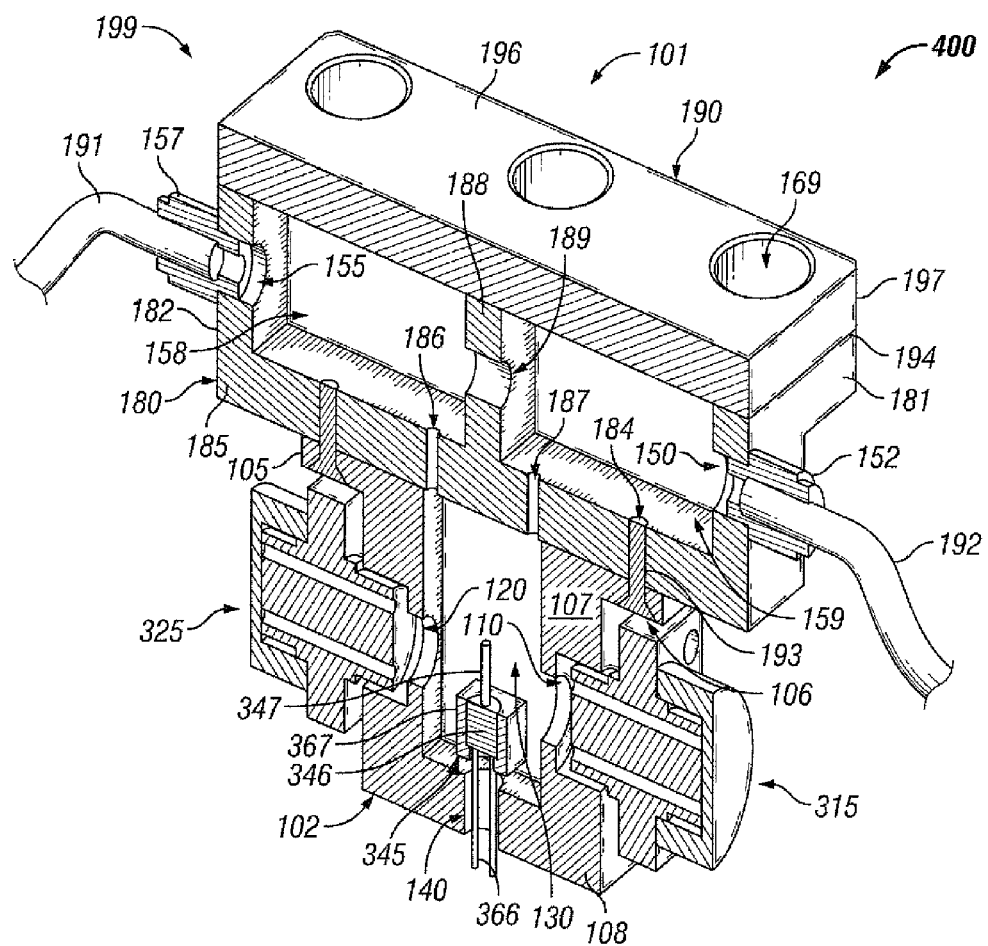
FIG. 4 shows a top-side perspective view of a portion of a gas sensor module that includes the gas sensor housing of FIG. 1 in accordance with certain example embodiments.

In this case, one coupling feature 184 is disposed adjacent to cavity portion 158, and the other coupling feature 184 is disposed adjacent to cavity portion 159. When a coupling feature 184 is an aperture, such as in this case, each coupling feature 184 can receive a fastening device (e.g., a bolt 193, as shown in FIG. 4 below) that is used to couple the top portion 199 to the bottom portion 102. A coupling feature 184 can also be disposed, in whole or in part, within another wall (e.g., side wall 182) of the top portion 199.

The characteristics (e.g., shape, size, configuration) of the coupling features 184 can be configured to correspond to the associated characteristics of coupling features (e.g., coupling features 106) of the bottom portion 102, described below. In such a case, the top portion 199 can be coupled to the bottom portion 102 in one or more certain orientations. The top portion 199 can include one or more features to accommodate the coupling features 184. For example, there can be mating threads disposed along the inner surface of the bottom wall 185 that forms the coupling feature 184.

In certain example embodiments, the top portion 199 of the housing 101 includes one or more features that interact with one or more other components of the housing 101 and/or an optical gas sensor. For example, as shown in FIGS. 1-2B, the top portion 199 can include an inlet tube coupling feature 150, an outlet tube coupling feature 155, a distribution channel 187, and a receiving channel 186. In such a case, the inlet tube coupling feature 150 can couple to the inlet tube, as shown below with respect to FIG. 4. The inlet tube coupling feature 150 can include one or more of a number of coupling features. For example, in this example, the inlet tube coupling feature 150 can be an aperture that traverses a side wall 182 of the top portion 199. The inlet tube is configured to deliver test gas into the cavity portion 159 of the top portion 199 of the housing 101.

To deliver the test gas from the cavity portion 159 of the top portion 199 to the cavity 130 of the bottom portion 102 of the housing 101, the top portion 199 can include one or more distribution channels 187. In such a case, the distribution channel 187 can include one or more features (e.g., side walls) sufficient to allow test gas to pass therethrough. The distribution channel 187 can be disposed, at least in part, in a wall (e.g., bottom wall 185) of the top portion 199. Further, the distribution channel 187 can be located adjacent to a portion (e.g., cavity portion 159) of the cavity of the top portion 199. In certain example embodiments, the distribution channel 187 is adjacent to the same portion of the cavity as the inlet tube coupling feature 150. For example, in this case, the distribution channel 187 and the inlet tube coupling feature 150 are each located adjacent to cavity portion 159 at different positions along a wall (or, in this case, different walls) of the top portion 199.

In some cases, the distribution channel 187 transports the test gas from the top portion 199 to the bottom portion 102 of the housing 101. For example, in this case, the distribution channel 187 is disposed in the bottom wall 185 of the top portion 199 of the housing 101. In certain example embodiments, the distribution channel 187 (or portions thereof) can include a partition, as with the partition 188 described above with respect to the cavity of the top portion 199, to help control the flow of the test gas as the test gas flows to the cavity 130 of the bottom portion 102.

To continue with the circulation process involving the test gas, once the test gas is tested inside the cavity 130 of the bottom portion 102, the resulting gas (called the tested gas) is removed from the cavity 130 of the bottom portion 102. To receive the tested gas by the top portion 199 from the bottom portion 102, the top portion 199 can include one or more receiving channels 186 that can include one or more features (e.g., side walls) sufficient to allow tested gas to pass therethrough. The receiving channel 186 can be disposed, at least in part, in a wall (e.g., bottom wall 185) of the top portion 199. Further, the receiving channel 186 can be located adjacent to a portion (e.g., cavity portion 158) of the cavity of the top portion 199. In certain example embodiments, the receiving channel 186 is adjacent to the same portion of the cavity as the outlet tube coupling feature 155, described below. For example, in this case, the receiving channel 186 and the outlet tube coupling feature 155 are each located adjacent to cavity portion 158 at different positions along a wall (or, in this case, different walls) of the top portion 199.

In some cases, the receiving channel 186 transports the tested gas from the bottom portion 102 of the housing 101 to the top portion 199. For example, in this case, the receiving channel 186 is disposed in the bottom wall 185 of the top portion 199 of the housing 101. In certain example embodiments, the receiving channel 186 (or portions thereof) can include a partition, as with the partition 188 described above with respect to the cavity of the top portion 199, to help control the flow of the tested gas as the tested gas flows from the cavity 130 of the bottom portion 102 to the cavity portion 158 of the top portion 199.

To complete the circulation process involving the tested gas, the outlet tube coupling feature 155 of the top portion 199 can couple to an outlet tube (described below with respect to FIG. 4). The outlet tube coupling feature 155 can include one or more of a number of coupling features. For example, in this example, the outlet tube coupling feature 155 can be an aperture that traverses a side wall 182 of the top portion 199. The outlet tube is configured to remove tested gas from the cavity portion 158 of the top portion 199 of the housing 101.

As discussed above, in certain example embodiments, the top portion 199 of the housing 101 can have one or more channels (e.g., distribution channel 186, receiving channel 187) disposed in the main body 180. Such channels can be used, for example, to inject test gas into and/or remove tested gas from the cavity 130 of the bottom portion 102 of the housing 101. Channel 187 can be disposed in a different location (relative to the location of channel 186) in the main body 180 of the top portion 199 of the housing 101. Each channel can have any of a number of features, shapes, sizes, and/or orientations. For example, in this case, channel 186 can include a channel wall 172 that is disposed in the main body 180 of the top portion 199 and that is substantially linear. The channel 186 in this case also has a first end 171 disposed at the outer surface of the bottom wall 185 and a second end 170 disposed at the inner surface of the bottom wall 185 (adjacent to the cavity portion 159).

Similarly, channel 187 can include a channel wall 177 that is disposed in the main body 180 of the top portion 199 and that is substantially linear. The channel 187 in this case also has a first end 176 disposed at the outer surface of the bottom wall 185 and a second end 175 disposed at the inner surface of the bottom wall 185 (adjacent to the cavity portion 158). In this case, channel 186 is substantially parallel with channel 187. The channel wall of a channel can be coated with one or more of a number of materials. In addition, or in the alternative, the channel wall of a channel can have a sleeve (e.g., a distribution tube, a receiving tube) or some similar component of the gas sensor module disposed therein.

The first end (e.g., first end 171, first end 176) of a channel can also be disposed at an inner surface of a side wall 182 of the main body 180 or at some other location on the top portion 199, depending on one or more of a number of factors, including but not limited to the characteristics (e.g., shape, size, orientation) of the top portion 199, and the location of one or more components (e.g., a gas injector, a gas collector) of the gas sensor module. A channel (e.g., distribution channel 186, receiving channel 187) can be linear, curved, angled, and/or have one or more of any other shapes. Similarly, a channel wall (e.g., channel wall 172, channel wall 177) of a channel can have any of a number of characteristics (e.g., size, cross-sectional shape, length, width) suitable for the gas sensor module.

In certain example embodiments, the top portion 199 of the housing 101 can include multiple components that are mechanically coupled to each other. For example, as shown in FIGS. 1-2B, the top plate 190 of the top portion 199 can be a separate component from the main body 180 of the top portion 199. In such a case, the top plate 190 can be coupled to the main body 180 in one or more of a number of ways (e.g., fixedly, removably, hingedly). In this example, the top plate 190 is removably coupled to the main body 180. Specifically, the top plate 190 of FIG. 1 includes a number of coupling features 195 (in this case, apertures) that align with and couple to, directly or indirectly, complementary coupling features 183 (also apertures in this case) disposed in a side extension 181 of the main body 180.

In this example, the coupling features 195 traverse at least a portion of the thickness (between the top surface 196 and the bottom surface 194) of the top plate 190. The thickness of the top plate 190 is substantially the same as the height of the side wall 197 of the top plate 190. Similarly, in this case, the coupling features 183 traverse at least a portion of the thickness of the side extensions 181 of the main body 180. In this case, as shown in FIG. 4 below, the coupling features 183 and the coupling features 195 are indirectly coupled to each other by coupling features 169, which in this case are fastening devices (e.g., screws, bolts).

As another example, the top plate 190 and/or the main body 180 of the top portion 199 of the housing 101 can be made of multiple pieces. Similarly, the bottom portion 102 can be made of multiple pieces. For example, the view of the top plate 190 the main body 180, and the bottom portion 102 shown in FIG. 1 can be actual pieces of those components that are coupled to mirror images of those components to form an substantial enclosure of cavity portion 158, cavity portion 159, and cavity 130. When the top portion 199 or the bottom portion 102 is made of multiple pieces, the multiple pieces can be substantially symmetrical to each other. Alternatively, the multiple pieces can have non-symmetrical shapes relative to each other.

In any case, when the various pieces of the top portion 199 and/or the various pieces of the bottom portion 102 abut against each other (couple to each other), the various cavities (or portions thereof) become substantially whole and continuous. Further, when the various pieces are coupled to each other, the associated coupling features (e.g., the inlet tube coupling feature 150, the outlet tube coupling feature 155, the tuning fork coupling feature 140 (described below), the distribution channel 187, the receiving channel 186) can be made whole. In such a case, one or more of these pieces can include additional coupling features to facilitate coupling those pieces to each other.

The bottom portion 102 can have at least one wall that forms the cavity 130. For example, in this case, the bottom portion 102 of the housing 101 includes a bottom wall 108 and a side wall 107. The cavity 130 formed the walls of the bottom portion 102 can have a shape and size sufficient to test the test gas distributed into the cavity 130 based on the other components (e.g., tuning fork, optical device) used to test the test gas. For example, as shown in FIGS. 1 and 3, the cavity 130 can be substantially rectangular parallelepiped in shape.

In certain example embodiments, the bottom portion 102 of the housing 101 includes one or more features that interact with one or more other components of the housing 101 and/or an optical gas sensor. For example, as shown in FIGS. 1 and 3, the bottom portion 102 can include a tuning fork coupling feature 140, an optical device coupling feature 110, and an optical device coupling feature 120.

The tuning fork coupling feature 140 (or portion thereof) can couple, directly or indirectly, to a tuning fork (e.g., tuning fork 345 of FIG. 4 below, tuning fork 545 of FIG. 5 below). The tuning fork coupling feature 140 can have a shape and size to host one or more of a number of tuning forks. The tuning fork coupling feature 140 can be disposed at any location along an inner surface of a wall (e.g., bottom wall 108) that forms the cavity 130. For example, as shown in FIGS. 1 and 3, the tuning fork coupling feature 140 can be disposed in the approximate center of the inner surface of the bottom wall 108 adjacent to the cavity 130. The tuning fork coupling feature 140 can include any of a number of features (e.g., a collar, a notch, a protrusion, a recess) to help in coupling the tuning fork with the tuning fork coupling feature 140. In addition, the tuning fork coupling feature 140 can be disposed along an inner surface of another wall (e.g., side wall 107) adjacent to the cavity 130.

In certain example embodiments, the optical device coupling feature 120 (or a portion thereof) can couple, directly or indirectly, to an optical device (e.g., optical device 325 of FIG. 4 below, optical device 525 of FIG. 5 below). The optical device coupling feature 120 can have a shape and size to host one or more of a number of optical devices. The optical device coupling feature 120 can be disposed at any location along an inner surface of a wall (e.g., side wall 107) that forms the cavity 130. For example, as shown in FIGS. 1 and 3, the optical device coupling feature 120 can be disposed in the inner surface of the side wall 107 at a particular lateral location relative to the tuning fork coupling feature 140 adjacent to the cavity 130. The optical device coupling feature 120 can include any of a number of features (e.g., a collar 122, a notch, a protrusion, a recess) to help in coupling an optical device with the optical device coupling feature 120. In addition, the optical device coupling feature 120 can be disposed along an inner surface of another wall (e.g., bottom wall 108) adjacent to the cavity 130.

Similarly, the optical device coupling feature 110 (or a portion thereof) can couple, directly or indirectly, to an optical device (e.g., optical device 315 of FIG. 4 below, optical device 515 of FIG. 5 below). The optical device coupling feature 110 can have a shape and size to host one or more of a number of optical devices. The optical device coupling feature 110 can be disposed at any location along an inner surface of a wall (e.g., side wall 107) that forms the cavity 130. For example, as shown in FIGS. 1 and 3, the optical device coupling feature 110 can be disposed in the inner surface of the side wall 107 at a particular lateral location relative to the tuning fork coupling feature 140 and to the optical device coupling feature 120, adjacent to the cavity 130. The optical device coupling feature 110 can include any of a number of features (e.g., a collar 112, a notch, a protrusion, a recess) to help in coupling an optical device with the optical device coupling feature 110. In addition, the optical device coupling feature 110 can be disposed along an inner surface of another wall (e.g., bottom wall 108) adjacent to the cavity 130.

In addition to, or in the alternative of, the tuning fork coupling feature 140, the optical device coupling feature 110, and/or the optical device coupling feature 120, one or more other features can be disposed in a wall (e.g., side wall 107, bottom wall 108) of the bottom portion 102 of the housing 101. Examples of such other features can include, but are not limited to, a light source coupling feature (for housing and/or coupling to a light source) and a power source coupling feature (for housing and/or coupling to a power source).

In cases where the bottom portion 102 has a top plate (e.g., similar to the top plate 190 of the top portion 199) or a top wall that at least substantially encloses the cavity 130, the bottom portion 102 can include one or more additional features, including but not limited to a distribution channel (e.g., similar to the distribution channel 187 of the top portion 199), and a receiving channel (e.g., similar to the receiving channel 186 of the top portion 199).

In certain example embodiments, the various coupling features (e.g., the optical device coupling feature 110, the optical device coupling feature 120, the tuning fork coupling feature 140) of the bottom portion 102 can be sized and/or arranged in a particular way, based on the characteristics of the components that couple to those coupling features, in order to achieve certain test results and/or to meet certain applicable standards. Similarly, some or all of the channels (e.g., distribution channel 187, receiving channel 186) of the top portion 199 can be sized and/or arranged in a particular way in order to achieve certain test results and/or to meet certain applicable standards.

In certain example embodiments, the bottom portion 102 of the housing 101 includes one or more of a number of coupling features 106 that allow the bottom portion 102 of the housing 101 to become coupled, directly or indirectly, to another portion (e.g., the top portion 199) of the housing 101 and/or to another component of the gas sensor module. Each coupling feature 106 can have any of a number of features and/or configurations. For example, in this case, each coupling feature 106 is an aperture that traverses the thickness of the laterally extended wall 105 of the bottom portion 102. In this case, there are two coupling features 106 that align with the coupling features 184 of the top portion 199 and are used to indirectly couple the top portion 199 and the bottom portion 102 of the housing 101 to each other using another coupling feature (e.g., coupling feature 193, as shown below in FIG. 4).

The coupling features 106 of the bottom portion 102 can have the same size and orientation compared to the shape and size of the coupling features 184 of the top portion 199. In this way, when the top portion 199 abuts against the bottom portion 102, the coupling features 184 and the coupling features 106 are aligned with each other so that one or more fastening devices can be disposed therein to couple the bottom portion 102 and the top portion 199 together.

In embodiments where the top portion 199 (or at least the main body 180) and the bottom portion 102 are formed from a single piece, so that the top portion 199 (or at least the main body 180) and the bottom portion 102 are permanently or fixedly coupled to each other, the coupling features 106 of the bottom portion 102 and/or the coupling features 184 of the top portion 199 can be omitted.

In certain example embodiments, a portion of the cavity of the top portion 199 of the housing 101 and/or the cavity 130 of the bottom portion 102 of the housing 101 can include one or more features that channel the flow of gas (e.g., test gas, tested gas) through that cavity or portion of the cavity. Examples of such features can include, but are not limited to, contoured inner surfaces of a wall and baffles. For example, cavity portion 159 can include baffles that channel test gas that flows from the inlet tube coupling feature 150 through the cavity portion 159 to the distribution channel 187. Such features can affect other aspects (e.g., turbulence, flow rate) of the test gas and/or tested gas.

FIG. 4 shows a top-side perspective view of a subassembly 400 of a gas sensor module that includes the gas sensor housing 101 of FIG. 1 in accordance with certain example embodiments. Referring to FIGS. 1-4, in addition to the housing 101, subassembly 400 of FIG. 4 includes an optical device 315 disposed in the optical device coupling feature 110, an optical device 325 disposed in the optical device coupling feature 120, a tuning fork 345 disposed in the tuning fork coupling feature 140, an inlet tube 192 disposed in the inlet tube coupling feature 150, and an outlet tube 191 disposed in the outlet tube coupling feature 155.

The optical device 315 coupled to the optical device coupling feature 110 can be an assembly of one or more components (e.g., lens, light source) that uses any type of optical and/or other technology. For example, optical device 315 can be a photodiode assembly. If the optical device 315 includes a lens, the lens can be a plano-convex lens that has a focus at some point in the cavity 130. The optical device 315 can be coupled directly or indirectly to the optical device coupling feature 110. For example, the optical device 315 can include, or can be coupled to, a SubMiniature version A (SMA) connector, which in turn is coupled to the optical device coupling feature 110.

If the optical device 315 includes a light source, the light source can generate light that is directed toward the cavity 130, either directly or indirectly (e.g., through a lens) of the optical device 315. The light generated and emitted by the light source can be of any suitable wavelength, depending on one or more of a number of factors, including but not limited to the gas being tested, the temperature, and the characteristics of the lens of the optical device 315. The light source of the optical device 315 can be coupled to a power source (e.g., a driver), which can provide power and/or control signals to the light source and/or other components of the optical device 315.

The light source can include one or more of a number of components, including but not limited to a light element (e.g., a light-emitting diode, a bulb) and a circuit board. If the optical device 315 includes a lens, the lens can be capable of receiving light (e.g., from a light source) and processing the light to create light that is transmitted to a particular location within the cavity 130. The optical device 315 can have any shape (e.g., sphere, semi-sphere, pyramid) and size that conforms to one or more contours of the optical device coupling feature 110.

The optical device 315 can be made of one or more suitable materials, including but not limited to silica and glass. In any case, the optical device 315 is resistant to corrosive materials, such as $H_2S$ gas. In order for the optical device 315 to transmit the light to a particular location within the cavity 130, a number of factors must be balanced. Such factors can include, but are not limited to, the orientation of the optical device 315, the material of the optical device 315, the position of the optical device 315 relative to the tuning fork 345 in the cavity 130, and the wavelength of the light. In certain example embodiments, a sealing member (e.g., a gasket, an o-ring, silicone) can be used to provide a barrier that prevents potentially corrosive materials in the cavity 130 from entering the optical device coupling feature 110.

The optical device 325 coupled to the optical device coupling feature 120 can be an assembly of one or more components (e.g., lens, light source) that uses any type of optical and/or other technology. The optical device 325 can be substantially the same as, or different than, the optical device 315. For example, optical device 325 can be a laser diode assembly. If the optical device 325 includes a lens, the lens can be a plano-convex lens that has a focus at some point in the cavity 130. The optical device 325 can be coupled directly or indirectly to the optical device coupling feature 120. For example, the optical device 325 can include, or can be coupled to, a SMA connector, which in turn is coupled to the optical device coupling feature 120. The optical device 325 can include one or more of a number of components, such as the components (e.g., lens, light source) described above for the optical device 315.

As discussed above, the cavity 130 of the bottom portion 102 can be formed by more than one piece. In such a case, the inner surface of the walls (e.g., side wall 107, bottom wall 108) of the pieces can be highly machined so that the junctions where the multiple pieces meet within the cavity 130 provide little to no seems that could impede the flow or the testing of the gas within the cavity 130.

In certain example embodiments, the light transmitted from an optical device (optical device 315, optical device 325), perhaps with the aid of a lens, is directed to particular point within the cavity 130. The particular point can be with respect to a portion of the tuning fork 345, described below. An example of such a particular point is approximately two-thirds up the length of a tine 347 (or between multiple tines 347) of the tuning fork 345.

The test gas that is distributed into the cavity 130 can include one or more elements (e.g., carbon, hydrogen) that can combine to form one or more compounds (e.g., methane). In some cases, the gas can also have impurities (e.g., $H_2S$) that can be detected, both in existence and in amount, using the optical gas sensor. As discussed above, the test gas can be injected into the cavity 130 through one or more channels (e.g., channel 187) disposed in the main body 180 of the top portion 199 of the housing 101, entering the cavity 130 through the second end 175 (also called a gas entry port 175) of the channel 187.

The positioning of the gas entry port 175 and/or the alignment of the channel wall 177 of the channel 187 can coincide with a reference point of or within the cavity 130. For example, in this case, the channel 187 is configured to direct the gas proximate to and along an inner surface of the inner wall 107, aligned with the optical device 315. Alternatively, the channel 187 can be configured to direct the gas at some other point or area of or within the cavity 130.

When the gas molecules interact with the light waves generated by an optical device (e.g., optical device 315, optical device 325) and directed into the cavity 130, the gas molecules become stimulated. Thus, the channel 187 is positioned and/or configured in such a way that the test gas emitted through the gas entry port 175 can more easily interact with the light waves within the cavity 130.

As discussed below, the tines 347 of the tuning fork 345, disposed in the tuning fork cavity 140, can be positioned such that the light emitted by an optical device into the cavity 130 is directed between the tines 347. The energy released by the gas molecules, stimulated by the light waves in the cavity 130, interacts with the tines 347 of the tuning fork 345. In such a case, the stimulated gas molecules change the frequency at which the tines 347 vibrate. The parameters of an optical device (or portions thereof, such as the laser) are selected so that only a particular gas can cause such interactions with the tines 347 of the tuning fork 345. In certain example embodiments, the light emitted by the optical device is directed between (in some cases, at a particular point between) the tines 347 of the tuning fork 345.

As discussed above, the tuning fork 345 (or portions thereof) can be made of quartz. The tuning fork 345, coupled to (e.g., disposed in) the tuning fork coupling feature 140 of the bottom portion 102 of the housing 101, can be any type of device that vibrates at one or more frequencies. The tuning fork 345 can have one or more components. For example, in this case, the tuning fork 345 has multiple (e.g., two) tines 347 and a base 346 from which the tines 347 extend. The tines 347 can be at least partially flexible, so that the shape of the tines 347 can change. When the shape of the tines 347 changes, the tines 347 can vibrate at a different frequency. The tuning fork 345 (including any of its components, such as the tines 347) can be made of any suitable material, including but not limited to quartz. In any case, the tuning fork 345 can be resistant to corrosive materials, such as $H_2S$ gas.

The tines 347 of the tuning fork 345 can be oriented in any of a number of suitable ways within the cavity 130. For example, the tines 347 can be substantially parallel to the inner surface of the side walls 107 that help form the cavity 130. In certain example embodiments, a sealing member (e.g., a gasket, an o-ring, silicone) (not shown) can be used to provide a barrier that prevents potentially corrosive materials in the cavity 130 from entering the tuning fork coupling feature 140. In certain example embodiments, the tines 347 of the tuning fork 345 are made of or coated with a material that is resistant to corrosive elements, such as $H_2S$.

The tines 347 of the tuning fork 345 can vibrate based on something other than the stimulated gas molecules within the cavity 130. For example, a driver (not shown) can be coupled to the tuning fork 345. In such a case, the driver can provide a vibration frequency to the tuning fork 345, causing the tines 347 to vibrate at a certain frequency. Such a frequency may be substantially similar to a frequency induced by a pure form (without any impurities) of the gas being stimulated within the cavity 130.

To measure the frequency at which the tines 347 of the tuning fork 345 are vibrating, one or more measuring devices can be used. For example, a receiver (not shown) can be coupled to the tuning fork 345. In such a case, the receiver can determine a vibration frequency to the tuning fork 345. Thus, when the vibration frequency of the tines 347 changes, the measured change can be directly correlated to an impurity in the test gas injected through the channel into the cavity 130.

The driver and/or the receiver can be coupled to the tuning fork 345 in one or more of a number of ways. For example, as shown in FIG. 4, an adapter 367 can be mechanically coupled to the base 346 of the tuning fork 345, and one or more electric conductors 366 can be coupled between the adapter 367 and the driver and/or the receiver. In certain alternative embodiments, wireless technology can be used to couple the driver and/or the receiver to the tuning fork 345.

In certain example embodiments, optical device 315 and optical device 325 each include a lens and are placed at opposite ends of the cavity 130 with the tines 347 of the tuning fork 345 in the direct linear path between the two lenses. Further, the focus of converging lenses of optical device 315 and optical device 325 lies substantially exactly in between the tines 347 of the tuning fork 345 and also at a height (e.g., two-thirds of the height of the tines 347) relative to the base 346 of the tuning fork 345. In such a case, optimal optical alignment can be achieved as all three elements (optical device 315, optical device 325, and tuning fork 345) are aligned along a central axis.

In some cases, if the two lenses of the optical devices have substantially the same focus, improved measurements of the test gas can be taken. For example, the optical alignment with a laser of one optical device (e.g., optical device 315) directed through its lens can be detected by a photo-diode of the other optical device (e.g., optical device 325) through its lens. Further, if the lenses of the optical devices are converging, maximum energy can be focused between the tines 347 of the tuning fork 345, creating a maximum interaction of a laser (light) with test gas molecules at that point, resulting in an increased sensitivity and improved measurements.

In certain example embodiments, the bottom portion 102 of the housing 101 has only a single optical device coupling feature. Alternatively, the bottom portion 102 of the housing 101 can have more than two optical device coupling features. When the bottom portion 102 of the housing 101 has two optical device coupling features, they can be aligned with each other at opposite ends of the cavity 130, as shown in FIG. 4. Alternatively, the two optical device coupling features can be disposed at any point with respect to each other in the cavity 130.

With respect to the top portion 199 of the housing 101, the inlet tube coupling feature 150 can be coupled, directly or indirectly, to an inlet tube 192. In this case, the inlet tube 192 has disposed on its distal end a threaded coupling 152 (a type of coupling feature). In such a case, the threaded coupling 152 is directly coupled to both the inlet tube coupling feature 150 and to the inlet tube 192. Similarly, the outlet tube coupling feature 155 can be coupled, directly or indirectly, to an outlet tube 191. In this case, the outlet tube 191 has disposed on its distal end a threaded coupling 157 (a type of coupling feature), which can be substantially the same as, or different than, the threaded coupling 152. In such a case, the threaded coupling 157 is directly coupled to both the outlet tube coupling feature 155 and to the outlet tube 191.

The inlet tube 192 receives test gas from some component (e.g., an inlet header) of the gas sensor or other external device, and the outlet tube 191 sends tested gas to component (e.g., an outlet header) of the gas sensor or other external device. Also, as discussed above, the top plate 190 is coupled to the main body 180 of the housing 101 using coupling features 169. In this case, the coupling features 169 are fastening devices (e.g., screws, bolts) that traverse the coupling features 195 of the top plate 190 and the coupling features 183 of the main body 180, where the coupling features 195 and the coupling features 183 are apertures.

Figure 5:
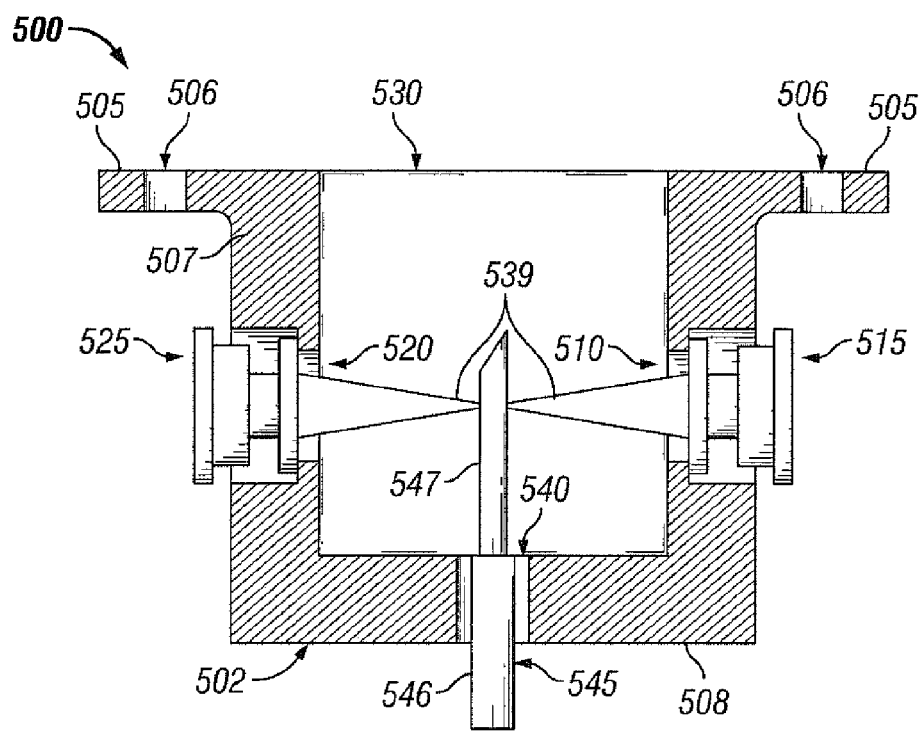
FIG. 5 shows a cross-sectional side view of a portion of another gas sensor module in accordance with certain example embodiments.

FIG. 5 shows a cross-sectional side view of a subassembly 500 of another gas sensor module in accordance with certain example embodiments. In this case, the subassembly 500 includes a tuning fork 545, an optical device 515, an optical device 525, and the bottom portion 502 of the housing. Referring to FIGS. 1-5, the tuning fork 545, the optical device 515, the optical device 525, and the bottom portion 502 of the housing of FIG. 5 are substantially the same as the tuning fork 345, the optical device 315, the optical device 325, and the bottom portion 102 of the housing 101 of FIGS. 1-4, except as described below. Unless stated otherwise below, a component (e.g., side wall 107, cavity 130) of FIGS. 1-4 is substantially the same as a corresponding component (e.g., side wall 507, cavity 530) of FIG. 5, where the last two digits of such component in FIGS. 1-4 and the corresponding component in FIG. 5 are the same.

In this case, the optical device 515 and the optical device 525 each have a lens (lens 510 and lens 520, respectively). The optical device 515 and the optical device 525 also have different shapes, sizes, and other components compared to the optical device 315 and the optical device 325 of FIG. 4. Further, the configuration of the tuning fork 545 of FIG. 5 is different than the configuration of the tuning fork 345 of FIG. 4. For example, the base 546 of the tuning fork 545 of FIG. 5 is not disposed in the cavity 530, and the tuning fork 545 does not include an adapter.

Example embodiments provide a number of benefits. Examples of such benefits include, but are not limited to, compliance with one or more applicable standards (e.g., IP65, IEC 60079-28, Zone 1 or Zone 2 compliance), ease in maintaining and replacing components, and more accurate and quicker detection and measurement of impurities in gases. The example housing described herein can reduce/control the effects of flow and/or turbulence of the test gas and/or the tested gas. Example embodiments can also allow for better alignment accuracy within the sensor head cavity so that the test gas can be more accurately tested. The shape, size, and other characteristics of the various components of a gas sensor module, including the example housing described herein, can be engineered to achieve optimal flow rate, minimal turbulence, optimal efficiency, and/or any of a number of other performance metric.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A housing for a gas sensor module, the housing comprising:
   a first portion comprising:
   at least one first wall forming a first cavity, wherein the first cavity comprises a first cavity portion and a second cavity portion;
   an inlet tube coupling feature disposed at a first location in the at least one first wall, wherein the first location is adjacent to the first cavity portion of the first cavity;
   an outlet tube coupling feature disposed in a second location in the at least one first wall, wherein the second location is adjacent to the second cavity portion of the first cavity;
   a distribution channel disposed at a third location in the at least one first wall, wherein the third location is adjacent to the first cavity portion of the first cavity; and
   a receiving channel disposed in a fourth location in the at least one first wall, wherein the fourth location is adjacent to the second cavity portion of the first cavity; and
   a second portion coupled to the first portion, wherein the second portion comprises:
   at least one second wall forming a second cavity; and
   a tuning fork coupling feature disposed at a fifth location in the at least one second wall, wherein the fifth location is adjacent to the second cavity.

2. The housing of claim 1, wherein the first cavity portion and the second cavity portion of the first cavity are separated by a partition.

3. The housing of claim 2, wherein the partition has at least one orifice that traverses therethrough.

4. The housing of claim 1, wherein the second portion further comprises:
   a first optical device coupling feature disposed at a sixth location in the at least one second wall, wherein the fifth location is adjacent to the second cavity.

5. The housing of claim 4, wherein the second portion further comprises:
   a second optical device coupling feature disposed at a seventh location in the at least one second wall, wherein the seventh location is adjacent to the second cavity.

6. The housing of claim 1, wherein the second portion further comprises:
   an additional distribution channel disposed at a sixth location in the at least one second wall, wherein the sixth location is adjacent to the second cavity, wherein the additional distribution channel is aligned with the distribution channel of the first portion; and
   an additional receiving channel disposed at a sixth location in the at least one second wall, wherein the sixth location is adjacent to the second cavity, wherein the additional receiving channel is aligned with the receiving channel of the first portion.

7. The housing of claim 1, wherein the at least one first wall comprises at least one housing coupling feature, and wherein the at least one second wall comprises at least one complementary housing coupling feature that couples to the at least one housing coupling feature of the first portion.

8. The housing of claim 1, further comprising:
a receiving tube disposed within the receiving channel of the first portion.

9. The housing of claim 1, further comprising:
a distribution tube disposed within the distribution channel of the first portion.

10. The housing of claim 1, wherein the first portion further comprises a first piece and a second piece, wherein the first cavity portion and the second cavity portion are formed when the first piece and the second piece are coupled to each other.

11. The housing of claim 10, wherein the first piece and the second piece are substantially symmetrical to each other.

12. The housing of claim 1, wherein the inlet tube coupling feature is configured to receive an inlet tube of a gas sensor module, and wherein the outlet tube coupling feature is configured to receive an outlet tube of the gas sensor module.

13. The housing of claim 1, wherein the tuning fork coupling feature is configured to receive a tuning fork of a gas sensor module.

14. The housing of claim 1, further comprising:
a cover coupled to the first portion of the housing, wherein the cover encloses at least a portion of the first cavity when the cover is coupled to the first portion.

15. The housing of claim 14, wherein the first portion of the housing is removably coupled to the cover and to the second portion of the housing.

16. A gas sensor, comprising:
a housing comprising;
at least one wall forming a first cavity and a second cavity, wherein the first cavity comprises a first cavity portion and a second cavity portion;
an inlet tube coupling feature disposed at a first location in the at least one wall, wherein the first location is adjacent to the first cavity portion of the first cavity;
an outlet tube coupling feature disposed in a second location in the at least one wall, wherein the second location is adjacent to the second cavity portion of the first cavity;
a tuning fork coupling feature disposed at a third location in the at least one wall, wherein the third location is adjacent to the second cavity;
a distribution channel disposed between the first cavity portion of the first cavity and the second cavity; and
a receiving channel disposed between the second cavity portion of the first cavity and the second cavity;
an inlet tube coupled to the inlet tube coupling feature;
an outlet tube coupled to the outlet tube coupling feature; and
a tuning fork coupled to the tuning fork coupling feature.

17. The gas sensor of claim 16, further comprising:
a first optical device coupled to a first optical device coupling feature, wherein the first optical device coupling feature is disposed in a fourth location in the at least one wall, wherein the fourth location is adjacent to the second cavity; and
a second optical device coupled to a second optical device coupling feature, wherein the second optical device coupling feature is disposed in a fifth location in the at least one wall, wherein the fifth location is adjacent to the second cavity.

18. The gas sensor of claim 16, wherein the first cavity portion and the second cavity portion of the first cavity are separated by a partition.

19. The gas sensor of claim 18, wherein the partition has at least one orifice that traverses therethrough.

20. The gas sensor of claim 16, wherein the housing further comprises a first housing portion and a second housing portion coupled to the first housing portion, wherein the first cavity is disposed within the first housing portion, and wherein the second cavity is disposed within the second housing portion.

* * * * *